United States Patent
Lee et al.

(10) Patent No.: US 12,350,401 B2
(45) Date of Patent: Jul. 8, 2025

(54) MESENCHYMAL STEM CELLS-HYDROGEL-BIODEGRADABLE OR MESENCHYMAL STEM CELLS-HYDROGEL-NONDEGRADABLE SUPPORT COMPOSITION FOR ALLEVIATING OR IMPROVING EPIDERMOLYSIS BULLOSA

(71) Applicant: ANTEROGEN CO., LTD., Seoul (KR)

(72) Inventors: Sung-Koo Lee, Seoul (KR); Mihyung Kim, Seoul (KR)

(73) Assignee: ANTEROGEN CO., LTD., Seoul (KR)

( * ) Notice: Subject to any disclaimer, the term of this patent is extended or adjusted under 35 U.S.C. 154(b) by 0 days.

(21) Appl. No.: 17/819,220

(22) Filed: Aug. 11, 2022

(65) Prior Publication Data

US 2022/0378982 A1 Dec. 1, 2022

Related U.S. Application Data

(63) Continuation of application No. 15/803,132, filed on Nov. 3, 2017, now abandoned, which is a
(Continued)

(30) Foreign Application Priority Data

Apr. 12, 2016 (KR) .......................... 10-2016-0044514

(51) Int. Cl.
  *A61L 27/38* (2006.01)
  *A61K 9/00* (2006.01)
  (Continued)

(52) U.S. Cl.
  CPC ........ *A61L 27/3813* (2013.01); *A61K 9/0014* (2013.01); *A61K 9/70* (2013.01);
  (Continued)

(58) Field of Classification Search
  CPC .. C12N 5/0062; C12N 5/0625; C12N 5/0665; C12N 5/0068; A61K 47/30; A61K 9/70;
  (Continued)

(56) References Cited

U.S. PATENT DOCUMENTS

| | | | |
|---|---|---|---|
| 8,460,713 B2 * | 6/2013 | Gammelsaeter | A61P 17/00 435/325 |
| 2016/0051722 A1 | 2/2016 | Lee et al. | |

FOREIGN PATENT DOCUMENTS

| | | |
|---|---|---|
| KR | 10-0345034 B1 | 4/2003 |
| KR | 10-1022884 B1 | 3/2011 |

(Continued)

OTHER PUBLICATIONS

Perdoni et al., "Preconditioning of mesenchymal stem cells for improved transplantation efficacy in recessive dystrophic epidermolysis bullosa", Stem Cell Research & Therapy, 2014, 5(6):121, 12 pages.
(Continued)

*Primary Examiner* — Sean C. Barron
(74) *Attorney, Agent, or Firm* — MH2 Technology Law Group, LLP

(57) ABSTRACT

Provided are a composition and a sheet, including a mesenchymal stem cells-hydrogel-biodegradable support or a mesenchymal stem cells-hydrogel-nondegradable support and a preparing method thereof. More specifically, in the sheet including a mesenchymal stem cells-hydrogel-biodegradable support or a mesenchymal stem cells-hydrogel-nondegradable support according to the present invention, the high-active mesenchymal stem cells may be applied to a wounded part of a patient with epidermolysis bullosa as it is without isolation using proteases, and in the culturing, an extracellular matrix such as collagen, laminin, fibronectin, and elastin secreted from the mesenchymal stem cells is wholly present on the hydrogel to have an advantageous effect that skin reproduction and re-epithelization abilities
(Continued)

are significantly excellent as compared with conventional dressing agents used for epidermolysis bullosa.

15 Claims, 13 Drawing Sheets

Related U.S. Application Data continuation-in-part of application No. PCT/KR2017/003982, filed on Apr. 12, 2017.

(51) Int. Cl.
| | |
|---|---|
| *A61K 9/70* | (2006.01) |
| *A61K 38/39* | (2006.01) |
| *A61K 47/30* | (2006.01) |
| *A61L 27/52* | (2006.01) |
| *A61L 27/54* | (2006.01) |
| *A61P 17/00* | (2006.01) |
| *C12N 5/00* | (2006.01) |
| *C12N 5/071* | (2010.01) |
| *C12N 5/0775* | (2010.01) |

(52) U.S. Cl.
CPC ............. *A61K 38/39* (2013.01); *A61K 47/30* (2013.01); *A61L 27/52* (2013.01); *A61L 27/54* (2013.01); *A61P 17/00* (2018.01); *C12N 5/0062* (2013.01); *C12N 5/0068* (2013.01); *C12N 5/0625* (2013.01); *C12N 5/0665* (2013.01); *A61L 27/3834* (2013.01); *A61L 2300/20* (2013.01); *A61L 2300/64* (2013.01)

(58) Field of Classification Search
CPC ....... A61K 9/0014; A61K 38/39; A61P 17/00; A61L 27/54; A61L 27/3813; A61L 27/52; A61L 27/3834; A61L 2300/20; A61L 2300/64

See application file for complete search history.

(56) References Cited

FOREIGN PATENT DOCUMENTS

| | | |
|---|---|---|
| KR | 10-1495281 B1 | 2/2015 |
| WO | 2015/138502 A1 | 9/2015 |
| WO | 2015/173206 A1 | 11/2015 |
| WO | 2016/004212 A1 | 1/2016 |

OTHER PUBLICATIONS

Lin et al., "Defining Stem and Progenitor Cells within Adipose Tissue", Stem Cells and Development, 2008, vol. 17, No. 6, pp. 1053-1063.

Strioga et al., "Same or Not the Same? Comparison of Adipose Tissue-Derived Versus Bone Marrow-Derived Mesenchymal Stem and Stromal Cells", Stem Cells and Development, 2012, vol. 21, No. 14, pp. 2724-2752.

El-Darouti et al., "Treatment of dystrophic epidermolysis bullosa with bone marrow non-hematopoeitic stem cells: a randomized controlled trial", Dermatologic Therapy, 2016, vol. 29, No. 2, pp. 96-100 (epub Oct. 5, 2015).

Xiang et al., "Ex vivo expansion and pluripotential differentiation of cryopreserved human bone marrow mesenchymal stem cells", Journal of Zhejiang University Science B, 2007, vol. 8, No. 2, pp. 136-146.

* cited by examiner

MESENCHYMAL STEM CELLS-HYDROGEL-BIODEGRADABLE OR MESENCHYMAL STEM CELLS-HYDROGEL-NONDEGRADABLE SUPPORT COMPOSITION FOR ALLEVIATING OR IMPROVING EPIDERMOLYSIS BULLOSA

REFERENCE TO RELATED APPLICATIONS

This application is a continuation of U.S. application Ser. No. 15/803,132 filed Nov. 3, 2017, which is a Continuation-In-Part (CIP) application of PCT/KR2017/003982 filed Apr. 12, 2017, which claims priority to KR Application 10-2016-0044514 filed Apr. 12, 2016, the entire disclosures of which are incorporated herein by reference.

TECHNICAL FIELD

The present invention relates to a composition and a sheet for alleviating or improving epidermolysis bullosa, containing high-active living mesenchymal stem cells which are attached and cultured to a biodegradable or nondegradable support by suspending the cultured mesenchymal stem cells in a hydrogel, and a preparing method thereof. Specifically, the present invention is to provide a composition, a sheet, and a preparing method thereof capable of expressing a clinically significant effect when applied to a wounded part of epidermolysis bullosa by increasing expression of collagen type VII and laminin-5. Therefore, the composition or sheet may be usefully used for alleviating or improving symptoms of a patient with epidermolysis bullosa.

BACKGROUND ART

Epidermolysis bullosa is a rare hereditary disease that causes pain in the skin and mucous membrane due to the blistering easily caused even by light trauma since the mutation of genes makes proteins which constitute epidermis, epidermis-dermis boundary, and upper papillary dermis. Patients with epidermolysis bullosa have no binding proteins to hold two layers to form blisters when a small friction occurs on the layer and then the patient experience pains corresponding to the third-degree burns. The epidermolysis bullosa includes epidermolysis bullosa simplex (EBS), junctional epidermolysis bullosa (JEB), dystrophic epidermolysis bullosa (DEB), and the like, and most of the patients are known as EBS. Mutation of kelatin generated in the skin is known to be a main cause of disease, and it is known that EBS includes autosomal dominant inheritance, JEB includes autosomal recessive inheritance, DEB includes dominant and recessive types.

Up to now, a method of modifying keratin mixtures produced in the skin, methods such as bone marrow transplantation, and the like have been studied, but there is no method for the full recovery of the disease available yet. Main treatment is only made with a symptomatic therapy for relieving symptoms or complications. It is the most important to prevent blisters from being infected. Most blisters are caused by some pressure or a friction, so, touching should be avoided, and when the blisters are caused, it is known that preventing excessive fluid loss and infection is important while relieving pains and minimizing discomfort. Painkillers may also be used to relieve pain while dressings are performed.

For patients with epidermolysis bullosa, an effective dressing is recommended to prevent blisters from infections. For example, in case of EB simplex, a soft silicone type dressing agent, a lipido-colloid type dressing agent, a foam type dressing agent, a hydrogel type dressing agent, a sheet hydrogel type dressing agent, a biosynthetic cellulose type dressing agent, a bordered type dressing agent, or a powder type dressing agent ise recommended. Also, in case of EBS Dowling Meara, a lipido-colloid type dressing agent, a polymer membrane type dressing agent, and a hydrofiber type dressing agent are recommended. Also, in case of junctional EB, a hydrogel impregnated gauze type dressing agent, a hydrofiber type dressing agent, a lipido-colloid type dressing agent, a soft silicone type dressing agent, a polymer membrane type dressing agent, a soft silicon foam type dressing agent, and a soft silicon foam type dressing agent having a super-adsorbent agent are recommended. Also, in the case of dystrophic EB, a soft silicon type dressing agent, a lipido-colloid type dressing agent, a foam type dressing agent with soft silicon, a soft silicon foam type dressing agent with a super-adsorbent agent, a foam type dressing agent, a polymer membrane type dressing agent, a super-adsorption type dressing agent, and a boundary type dressing agent are recommended (see Denyer J, Pillay E. Best practice guidelines for skin and wound care in epidermolysis bullosa. International Consensus. DEBRA, 2012).

Regarding the dressing for healing wounds, there are patents available such as a patent (Korean Patent Registration No. 345,034) for a dressing agent for healing wounds in a form of a polyurethane foam which enhances biocompatibility and promotes absorption of secretions at the wounded sites by introducing a hydrophilic group, a patent (Korean Patent Registration No. 1,022,884) for a polyurethane foam dressing agent including a drug layer, and the like.

In case of dressing agents in the related art are used, it is more advantageous in alleviating irritation or facilitating the absorption of the eluate from the blister site when applied to a wounded site of epidermolysis bullosa. However, there are no known techniques for a dressing agent exhibits skin regeneration effects without irritation when the dressing agent is applied to a wounded site of epidermolysis bullosa patients.

Meanwhile, it is known that collagen type VII or collagen alpha-1 chain is a protein encoded by a COL7A1 gene and associated with dystrophic epidermolysis bullosa when the gene is mutated, and even though there is no mutation, it has been reported that an autoimmune response to collagen type VII may cause a disease called epidermolysis bullosa. Also, the collagen type VII is also known to interact with laminin-5 and fibronectin. In addition, a study was reported in Italy, in which stem cells containing a calibrated laminin-5 gene were transplanted into a femoral lesion of a patient with junctional epidermolysis bullosa through skin transplantation to achieve a blister-free clinical effect. Therefore, it can be seen that collagen type VII and laminin-5 play a very important role to alleviate or improve epidermolysis bullosa.

An object of the present invention is to provide a composition and a sheet for alleviating or improving epidermolysis bullosa, containing high-active living mesenchymal stem cells which are attached and cultured to a biodegradable or nondegradable support by suspending the cultured mesenchymal stem cells in a hydrogel, and a preparing method thereof. Specifically, an object of the present invention is to provide a composition, a sheet, and a preparing method thereof capable of expressing a clinically significant effect when applied to a wounded part of epidermolysis bullosa by increasing expression of collagen type VII and laminin-5.

DISCLOSURE

Technical Problem

The present invention has been made in an effort to provide a composition or a sheet for alleviating or improving epidermolysis bullosa including high-active mesenchymal stem cells for obtaining a clinically effective therapeutic effect and a preparing method thereof, which is used as a dressing agent for applying mesenchymal stem cells isolated from any one selected from the group consisting of human adipose, bone marrow, skin, blood vessels, muscles, brain, blood, placenta, dental pulp and umbilical cord blood to an affected area of epidermolysis bullosa.

Technical Solution

In order to achieve the objects, the present invention provides a composition and a sheet for alleviating or improving epidermolysis bullosa, including a mesenchymal stem cells-hydrogel-biodegradable or nondegradable support, more specifically, a mesenchymal stem cells-hydrogel-nondegradable support, and a preparing method thereof.

The mesenchymal stem cells are antilogous or allergenic cells that are positive for CD29, CD44, CD73, CD90, and CD105 and negative for CD34 and CD45.

In one embodiment according to the present invention, the support may use a biodegradable polymer support selected from the group consisting of poly-gamma-glutei acid (PGA), poly lactic acid (PLA), PGA/PLA, viral mesh, human placental membrane, bovine placental membrane, pig collagen, chitin, chatoyant, fibronectin and dextrin, or may use a nondegradable support such as sterilized no woven fabrics, polyethylene terephthalate (PET) films, polyethylene (PE) films, polypropylene (PP) films, polyurethane films, net type polyurethane films, or polyurethane coated with soft silicon on a single surface, or a combination thereof, for example, PGA/nonwoven fabric, PLA/nonwoven fabric, and PGA/PLA/nonwoven fabric.

In one embodiment according to the present invention, the hydrogel may be selected from the group consisting of fibrin glue, hyaluronic acid or derivatives thereof, gelatin, collagen, alginic acid, cellulose and pectin, and in this case, the concentration of fibrinogen forming fibrin glue may be 0.5 to 60 mg/mL, specifically 0.5 to 45 mg/mL, more specifically 0.5 to 30 mg/mL, much more specifically 0.5 to 20 mg/mL, and much more specifically 0.5 to 10 mg/mL.

In one embodiment according to the present invention, in order to prepare the sheet for alleviating or improving epidermolysis bullosa, the method includes proliferating stem cells of 20,000 or more and more specifically 20,000 to 400,000 per 1 $cm^2$ of the support by mixing the stem cells with the hydrogel to evenly coat 1,000 to 10,000 stem cells per 1 $cm^2$ of the support and culturing the stem cells in a medium containing at least one selected from the group consisting of FBS, and bFGF or EGF.

Advantageous Effects

According to the present invention, the composition or sheet for alleviating or improving epidermolysis bullosa, containing the mesenchymal stem cells-hydrogel-biodegradable support or nondegradable support increases the expression of specifically, collagen type VII and laminin-5 to express a clinically significant effect when being applied to the wounded part of epidermolysis bullosa.

Further, in the composition or sheet containing high-active mesenchymal stem cells, the high-active mesenchymal stem cells may be applied to a wounded part of a patient with epidermolysis bullosa as it is without isolation (selection) using proteases, and in the culturing, an extracellular matrix such as collagen, laminin, fibronectin, and elastin secreted from the mesenchymal stem cells is wholly present on the hydrogel to have an advantageous effect that skin reproduction and re-epithelization abilities are significantly excellent when the composition or sheet is applied to the wounded part of the patient with epidermolysis bullosa as compared with conventional therapeutic agents.

More specifically, the mesenchymal stem cells-hydrogel-support according to the present invention keep a form of fibroblasts even in a serum-free medium, and the cells survive 90% or more after 1 week elapses and thus the survival time is significantly increased as compared with a conventional stem cell therapeutic agent. Also, when thawing after freezing, the shape and the strength of the sheet are kept as it is and the cells in the sheet also survive 95% or more and long-term freezing at −80° C. is enabled without damage of the cells as a main active ingredient, and even when 1 year or more elapses when long-term freezing, the cells survive 95% or more when thawing. Further, various growth factors and cytokines promoting cell proliferation and angiogenesis are continuously secreted, various types of extracellular matrixes containing collagen type VII and laminin-5 are secreted in large amount, and the secreted extracellular matrixes are left in the hydrogel and applied to the wounded part to provide various substrates, thereby facilitating treatment of epidermolysis bullosa. Also, even if the inflammation occurs in the wounded part without causing the immune response, a secretion amount of TNF-α which is secreted by immune cells in large amount to increase immunoreactivity is significantly reduced to alleviate the inflammation, thereby helping in healing blisters and inflammation in patients with epidermolysis bullosa. Specifically, the expression of collagen type VII is significantly increased, thereby promoting tissue reproduction and re-epithelization.

DETAILED DESCRIPTION OF THE INVENTION

Figure 1A:
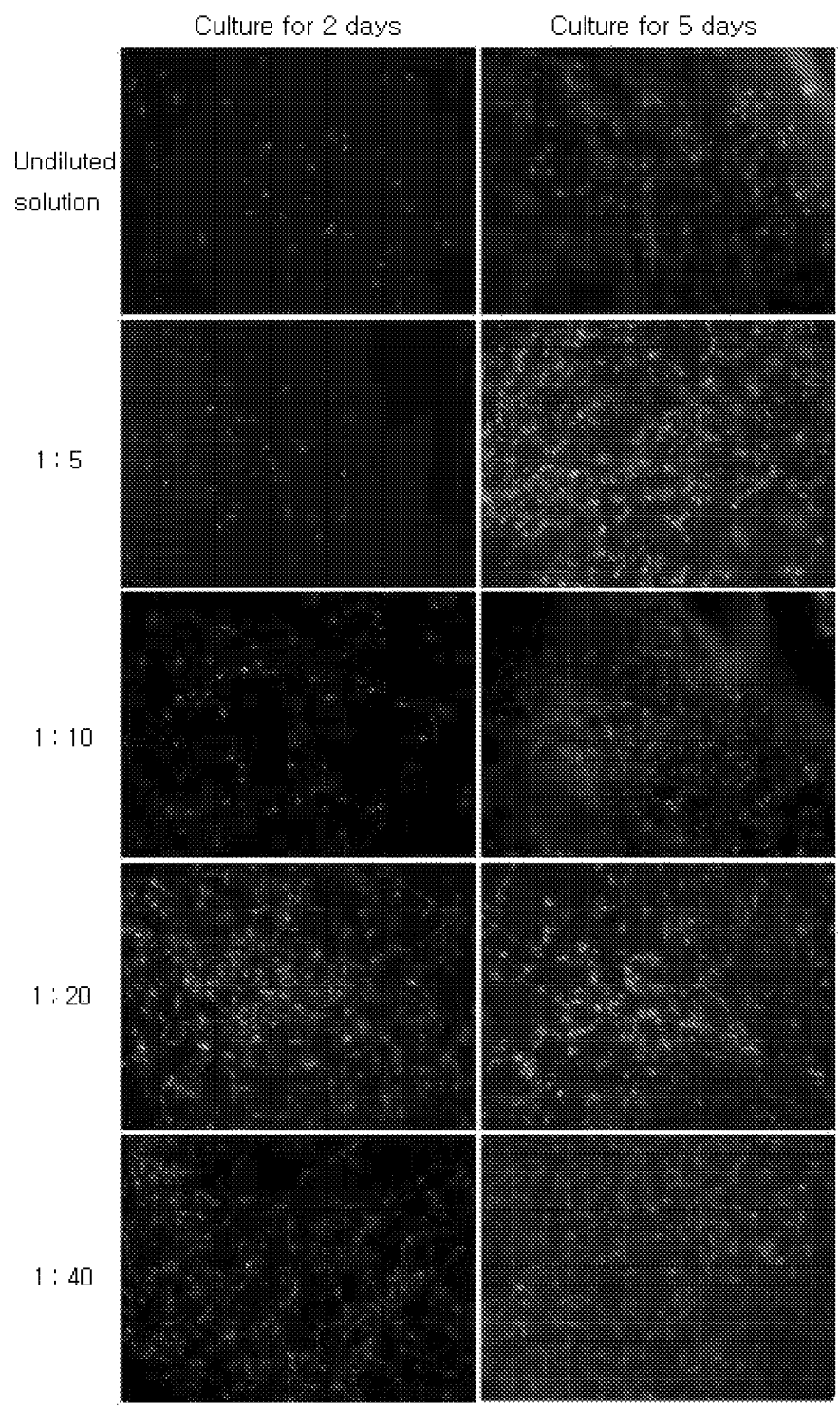
FIG. 1A is a fluorescence microscope photograph obtained by observing a form of mesenchymal stem cells derived from the human adipose which are cultured by mixing a fibrinogen undiluted solution and a fibrin gel prepared by a solution diluted stepwise and stained with AO/EtBr (400× magnification). Concentrations when the final fibrin glue is formed by mixing the dilution rate of the fibrinogen and a cell suspension containing thrombin at a ratio of 1:1 are expressed in parentheses.

In order to achieve the objects, the present invention provides a composition and a sheet for alleviating or improving epidermolysis bullosa, including a mesenchymal stem cells-hydrogel-biodegradable or nondegradable support, and a preparing method thereof.

Hereinafter, the present invention will be described in more detail.

The present invention provides a preparing method of a sheet for alleviating or improving epidermolysis bullosa, including: (a) obtaining a mesenchymal stem cells-hydrogel-support by attaching mesenchymal stem cells to (i) at least one kind of support selected from the group consisting of biodegradable supports and nondegradable supports; (ii) at least two kinds of nondegradable supports; or (iii) a combination of at least one kind of support and at least one kind of nondegradable support using a hydrogel; and (b) culturing the mesenchymal stem cells-hydrogel-support obtained in step (a) in a growth medium. Herein, the growth medium is a medium including fetal bovine serum (FBS) and at least one factor selected from the group consisting of a basic fibroblast growth factor (bFGF), an epidermal growth factor (EGF), a transforming growth factor beta-1 (TGF-beta1), a platelet-derived growth factor (PDGF), a vascular endothelial growth factor (VEGF), a hepatocyte growth factor (HGF) and an insulin-like growth factor (IFG-1), the hydrogel is at least one selected from the group consisting of fibrin glue, hyaluronic acid, gelatin, collagen, alginic acid, cellulose and pectin, the biodegradable support is selected from the group consisting of poly-gamma-glutamic acid (PGA), poly lactic acid (PLA), vicryl mesh, human placental membrane, bovine placental membrane, pig collagen, chitin, chitosan, fibronectin and dextran, and the nondegradable support is selected from the group consisting of sterilized nonwoven fabrics, polyethylene terephthalate (PET) films, polyethylene (PE) films, polypropylene (PP) films, polyurethane films, net type polyurethane films, and polyurethane coated with soft silicon on a single surface.

More specifically, the present invention provides a preparing method of a sheet for alleviating or improving epidermolysis bullosa, including: (a1) at least 2-subculturing mesenchymal stem cells in a growth medium; (a2) obtaining a mesenchymal stem cells-hydrogel-support by attaching the cultured mesenchymal stem cells to (i) at least one kind of support selected from the group consisting of biodegradable supports and nondegradable supports; (ii) at least two kinds of nondegradable supports; or (iii) a combination of at least one kind of support and at least one kind of nondegradable support using a hydrogel; and (b) culturing the mesenchymal stem cells-hydrogel-support obtained in step (a2) in a growth medium. Herein, the growth medium is a medium including fetal bovine serum (FBS) and at least one factor selected from the group consisting of a basic fibroblast growth factor (bFGF), an epidermal growth factor (EGF), a transforming growth factor beta-1 (TGF-beta1), a platelet-derived growth factor (PDGF), a vascular endothelial growth factor (VEGF), a hepatocyte growth factor (HGF) and an insulin-like growth factor (IFG-1), the hydrogel is at least one selected from the group consisting of fibrin glue, hyaluronic acid, gelatin, collagen, alginic acid, cellulose and pectin, the biodegradable support is selected from the group consisting of poly-gamma-glutamic acid (PGA), poly lactic acid (PLA), vicryl mesh, human placental membrane, bovine placental membrane, pig collagen, chitin, chitosan, fibronectin and dextran, and the nondegradable support is selected from the group consisting of sterilized nonwoven fabrics, polyethylene terephthalate (PET) films, polyethylene (PE) films, polypropylene (PP) films, polyurethane films, net type polyurethane films, and polyurethane coated with soft silicon on a single surface.

In one embodiment according to the present invention, the factor included in the growth medium may be more specifically, a basic fibroblast growth factor (bFGF), an epidermal growth factor (EGF), or a combination thereof.

In one embodiment according to the present invention, the mesenchymal stem cells are autologous or allogenic cells that are positive for CD29, CD44, CD73, CD90, and CD105 and negative for CD34 and CD45.

In one embodiment according to the present invention, in order to prepare the sheet for alleviating or improving epidermolysis bullosa, the method includes proliferating stem cells of 20,000 or more and more specifically 20,000 to 400,000 per 1 $cm^2$ of the support by mixing the stem cells with the hydrogel to evenly coat 1,000 to 10,000 stem cells per 1 $cm^2$ of the support and culturing the stem cells in a medium containing at least one selected from the group consisting of FBS, bFGF and EGF.

In one embodiment according to the present invention, in step (c), the method further includes (c) activating the cells by additionally performing at least one stimulation selected from the group consisting of physical stimulation, hypoxic stimulation, mitogen stimulation, and inflammatory factor stimulation such as IFN-gamma. In particular, in the case of tissues damaged by epidermolysis bullosa, since blood vessels are destroyed or a function is deteriorated, oxygen supply is not smooth and chronic inflammation may exist, stem cells administered to the damaged tissues are activated by hypoxic stress and inflammatory factors and the secretion of growth factors and cytokines is rapidly increased. Accordingly, it is possible to prepare the composition or sheet including high-active stem cells which secrete growth factors and cytokines at a high concentration by treating hypoxic stress, mitogens or inflammatory factors in the preparing of the support sheet.

In one embodiment according to the present invention, the hydrogel may use fibrin glue, hyaluronic acid, gelatin, collagen, alginic acid, cellulose or pectin, but is not limited thereto. When fibrin glue is used as the hydrogel, the concentration of fibrinogen forming fibrin glue may be 0.5 to 60 mg/mL, specifically 0.5 to 45 mg/mL, more specifically 0.5 to 30 mg/mL, much more specifically 0.5 to 20 mg/mL, much more specifically 0.5 to 10 mg/mL, and much more specifically 0.5 to 5 mg/mL, and thrombin may be included at a concentration of 1 to 50 I.U./mL, specifically 1 to 30 I.U./mL, and more specifically 5 to 20 I.U./mL.

In one embodiment according to the present invention, the stem cells-hydrogel sheet may be prepared by only the hydrogel itself, but the hydrogel has a low strength and may easily be torn by mechanical/physical force, and thus there are disadvantages that the size of the sheet is limited and careful attention in use is required. When attaching the mesenchymal stem cells-hydrogel to the biodegradable support or the nondegradable support, the support enhances the strength of the mesenchymal stem cells-hydrogel and makes manipulation easier.

In one embodiment of the present invention, the biodegradable support may be one kind or a combination of two or more kinds selected from the group consisting of poly-gamma-glutamic acid (PGA), poly lactic acid (PLA), vicryl mesh, human placental membrane, bovine placental membrane, pig collagen, chitin, chitosan, fibronectin and dextran, and the nondegradable support may be one kind or a combination of two or more kinds selected from the group consisting of sterilized nonwoven fabrics, polyethylene terephthalate (PET) films, polyurethane films, net type polyurethane films, polyurethane films coated with soft silicon on a single surface, polyethylene (PE) films, and polypropylene (PP) films, but is not limited thereto.

In one embodiment of the present invention, a combination of two or more nondegradable supports may be used, but is not limited thereto.

In one embodiment of the present invention, a combination of one or more biodegradable supports and nondegradable supports may be used as the support. For example, a polyurethane film, a net type polyurethane film, a polyurethane film coated with soft silicon on a single surface, PLA/nonwoven fabric, or PGA/PLA/nonwoven fabric may be used, but is not limited thereto.

In one embodiment of the present invention, in step (b), the method may further include (d) adding and freezing the mesenchymal stem cells-hydrogel-support in a freezing preservative containing 1 to 20 w/v % DMSO and 1 to 80 w/v % human serum albumin, and herein, when thawing after freezing, a survival rate of the mesenchymal stem cells is 70% or more.

In one embodiment of the present invention, when the mesenchymal stem cells-hydrogel-support composition according to the present invention is frozen and thawed, after 1 week, 1 month, 2 months, 3 months, 4 months, 5 months, 6 months, 7 months, 8 months, 9 months, 10 months, 11 months, and 12 months, the survival rate of the mesenchymal stem cells may be 70% or more, 75% or more, 80% or more, 85% or more, 90% or more, 91% or more, 92% or more, 93% or more, 94% or more, 95% or more, 96% or more, 97% or more, 98% or more, and 99% or more, more specifically, 90% or more and 95% or more after 12 months.

Another embodiment of the present invention provides a composition for alleviating or improving epidermolysis bullosa, containing mesenchymal stem cells and a hydrogel; and at least one support selected from the group consisting of biodegradable supports and nondegradable supports or a combination of at least one biodegradable support and at least one nondegradable support.

In one embodiment according to the present invention, the hydrogel may be at least one selected from the group consisting of fibrin glue, hyaluronic acid, gelatin, collagen, alginic acid, cellulose and pectin, but is not limited thereto. When the fibrin glue is used as the hydrogel, the concentration of fibrinogen forming the fibrin glue may be 0.5 to 60 mg/mL, specifically 0.5 to 45 mg/mL, more specifically 0.5 to 30 mg/mL, much more specifically 0.5 to 20 mg/mL, much more specifically 0.5 to 10 mg/mL, and much more specifically 0.5 to 5 mg/mL, and thrombin may be included at a concentration of 1 to 50 I.U./mL, specifically 1 to 30 I.U./mL, and more specifically 5 to 20 I.U./mL.

In one embodiment of the present invention, the biodegradable support may be one kind or a combination of two or more kinds selected from the group consisting of poly-gamma-glutamic acid (PGA), poly lactic acid (PLA), vicryl mesh, human placental membrane, bovine placental membrane, pig collagen, chitin, chitosan, fibronectin and dextran, and the nondegradable support may be one kind or a combination of two or more kinds selected from the group consisting of sterilized nonwoven fabrics, polyethylene terephthalate (PET) films, polyethylene (PE) films, polypropylene (PP) films, polyurethane films, net type polyurethane films, and polyurethane coated with soft silicon on a single surface, but the present invention is not limited thereto.

In one embodiment of the present invention, a combination of two or more nondegradable supports may be used, but is not limited thereto.

In one embodiment of the present invention, a combination of one or more biodegradable supports and nondegradable supports may be used as the support. For example, a polyurethane film, a net type polyurethane film, a polyurethane film coated with soft silicon on a single surface, PLA/nonwoven fabric, or PGA/PLA/nonwoven fabric may be used, but is not limited thereto.

Yet anther embodiment of the present invention provides a sheet for alleviating or improving epidermolysis bullosa, containing the composition as an active ingredient.

In one embodiment of the present invention, the epidermolysis bullosa may be selected from the group consisting of epidermolysis bullosa, acantholysis bullosa, acanthosis bullosa, epidermolysis bullosa acquisita, epidermolysis bullosa hereditaria, epidermolysis bullosa letalis, epidermolysis bullosa tarda, epidermolysis hereditaria tarda, hyperplastic epidermolysis bullosa, keratolysis, localized epidermolysis bullosa, non-scarring epidermolysis bullosa, polydysplastic epidermolysis bullosa, scarring bullosa, simplex epidermolysis bullosa, Weber-Cockayne disease, Dowling-Meara syndrome, Goldscheider's disease, Hallopeau-Siemens disease, Heinrichsbauer syndrome, Herlitz syndrome, and Kobner's disease.

In one embodiment of the present invention, the mesenchymal stem cells may be isolated from fat, bone marrow, or umbilical cord blood.

In one embodiment of the present invention, more specifically, the method may further include:

(a1) subculturing mesenchymal stem cells in a growth medium containing fetal bovine serum (FBS) and a basic fibroblast growth factor (bFGF) or an epidermal growth factor (EGF) as a growth factor two times or more;

(a2) attaching the cultured mesenchymal stem cells to a biodegradable or nondegradable support or a combination thereof using a hydrogel;

(b) culturing the mesenchymal stem cells-hydrogel-biodegradable or nondegradable support in step (a2) in the medium containing FBS and bFGF or EGF as a growth factor for about 5 days to prepare a sheet;

(c) activating cells by additionally performing physical stimulation, hypoxic stimulation, mitogen stimulation, and inflammatory factor stimulation when culturing in step (b);

(d) washing the mesenchymal stem cells-hydrogel-biodegradable or nondegradable support sheet in step (b) or (c) with a medium from which the FBS and the bFGF or EGF as a growth factor are removed;

(e) freezing the mesenchymal stem cells-hydrogel-biodegradable or nondegradable support sheet in step (b) in a freezing preservative containing 10% DMSO and 5% human serum albumin;

(f) removing the freezing preservative by thawing the frozen mesenchymal stem cells-hydrogel-biodegradable or nondegradable support sheet and washing the sheet with physiological saline; and (g) attaching the sheet to an applicable site after cutting the sheet according to a size of a wounded part requiring dressing in the wounded part of a patient with epidermolysis bullosa, and further include (h) covering the sheet with another dressing.

The method will be described in more detail as follows.

In step (a1), mesenchymal stem cells isolated from human adipose tissues may be used, and in this case, a method of isolating the mesenchymal stem cells isolated from human adipose tissues and subculturing the mesenchymal stem cells two times or more is disclosed in a prior art (Korean Patent Registration No. 1,328,604) and may effectively obtain a large amount of mesenchymal stem cells within a short time by culturing cells using a growth medium. According to the prior art, the human adipose-derived mesenchymal stem cells subcultured two times or more are attached to a plastic culture container to keep a form of fibroblasts and are positive for CD10, CD13, CD29, CD44, CD59, CD71, CD90, CD105 and Oct4 and negative for CD34, CD45, CD104, CD106 and Stro-1. Also, the human adipose-derived mesenchymal stem cells have ability to differentiate into adipocytes, bone cells, chondrocytes, muscle cells, and neurons in vitro as stem cells. Also, the human adipose-derived mesenchymal stem cells secrete a variety of growth factors such as VEGF, HGF, TGF-β1, NGF, and IGF and have immunoregulatory ability, and thus, technologies applied to treatment of various diseases have been developed.

In step (a2), the human adipose-derived mesenchymal stem cells subcultured two times or more in step (a1) are treated with trypsin or dispase to make a single cell, suspended in the hydrogel, and then evenly sprayed at a concentration of about 5,000/cm$^2$ to be attached to the biodegradable or nondegradable support fabric. Thereafter, the human adipose-derived mesenchymal stem cells are cultured for 3 to 7 days using the growth medium containing 10% FBS and EGF or bFGF. The hydrogel used in the embodiment of the present invention is a fibrin gel, but is not limited thereto, and may further include collagen, hyaluronic acid, gelatin, alginic acid, cellulose, and pectin.

Further, the biodegradable support used in the embodiment of the present invention is vicryl mesh or bovine placental membrane and the nondegradable support is sterilized gauze, a polyurethane film, a net type polyurethane film, a soft silicone coated polyurethane on a single surface, or a PET film, but are not limited thereto, and may use PGA/nonwoven fabric, PGA/PLA/nonwoven fabric, a human placental membrane, a collagen membrane, and the like.

In the present invention, the hydrogel primarily performs a function of attaching the mesenchymal stem cells to the biodegradable or nondegradable support fabric or the polyurethane film, the net type polyurethane film, the soft silicone coated polyurethane on a single surface, the PET film, the PE film, or the PP film and secondarily provides a substrate to the mesenchymal stem cells as attachable cells to attach the cells to the substrate, thereby providing an environment that can survive stably. Further, the hydrogel contains a large number of three-dimensional network pores, and provides an environment in which FBS, bFGF, or EGF contained in the culture medium passes through the network structure to act on the cells and may proliferate the cells. The hydrogel has a major influence on the shape and the growth rate of cells because the size, hardness and decomposition rate of the network structure depend on the prepared concentration. In the embodiment of the present invention, the growth rate of the mesenchymal stem cells is increased, while the proper hardness of the gel is maintained by using the fibrin gel at a final concentration of 0.5 to 10 mg/mL.

In step (b), in the mesenchymal stem cells-hydrogel-biodegradable or nondegradable support sheet, the mesenchymal stem cells are rapidly proliferated and increased four times or more for 3 to 7 days and 20,000 or more cells per cm² may be included.

In the present invention, the cells proliferated in the hydrogel express CD29, CD44, CD73, CD90, CD105 which are characteristic of the adipose-derived mesenchymal stem cells and may secrete various growth factors including VEGF and HGF. Also, the cells have inhibition ability of TNF-α and IFN-γ, which are representative inflammatory factors secreted from immune cells. That is, the cells cultured in the hydrogel maintain characteristics of the mesenchymal stem cells.

Also, in step (b), hypoxic stress, mitogen treatment, and inflammatory factor (IFN-γ) treatment may be used in combination. In the case of tissues damaged by epidermolysis bullosa, since blood vessels are destroyed or a function is deteriorated, oxygen supply is not smooth and chronic inflammation may exist, stem cells administered to the damaged tissues are activated by hypoxic stress and inflammatory factors and the secretion of growth factors and cytokines is rapidly increased.

As described above, the present invention provides a preparing method of a sheet including high-active stem cells secreting growth factors and cytokines at a high concentration by treating hypoxic stress, mitogens or inflammatory factors in the preparing of the adipose-derived mesenchymal stem cells-hydrogel-biodegradable or nondegradable support sheet.

Further, the adipose-derived mesenchymal stem cells-hydrogel-biodegradable or nondegradable support sheet prepared according to the present invention has excellent therapeutic ability because the high-active stem cells may be applied to the wounded part of a patient with excellent epidermolysis bullosa as it is without isolation using protease. Also, since there is no isolation using protease, in the culturing, an extracellular matrix such as collagen, laminin, fibronectin, and elastin secreted from the mesenchymal stem cells is wholly present on the hydrogel, thereby further promoting an effect of alleviating or improving epidermolysis bullosa.

As described above, in step (a2) of the present invention, the stem cells-hydrogel sheet may be prepared only by the hydrogel itself. However, since the hydrogel is low in strength and easily torn by mechanical/physical force, the size of the sheet is limited and careful attention is required in use. On the other hand, according to the present invention, when a stem cells-hydrogel is attached to a biodegradable or nondegradable support, the support enhances the strength of the stem cells-hydrogel to be easily manipulated. In addition, when the thickness of the sheet is 0.1 to 2 mm, the sheet is prevented from being torn when applied to the wounded part, and sufficient cell count is included in the sheet, thereby improving the therapeutic effect.

In step (d) of the present invention, the adipose-derived mesenchymal stem cells-hydrogel-biodegradable or nondegradable support sheet is washed 2 to 3 times with physiological saline to remove FBS as an animal-derived ingredient and may be washed in a serum-free DMEM medium in order to completely remove the FBS. In the process, the FBS is removed to minimize side effects that may be caused by the animal-derived ingredient when the sheet is applied to the human body.

The present invention includes a method of freezing the adipose-derived mesenchymal stem cells-hydrogel-biodegradable or nondegradable support sheet. The sheet is added with a freezing preservation configured by a solution of 10% DMSO and 5% human serum albumin to be sufficiently immersed in a Cryovac, sealed, and then stored at −80° C. Generally, it is known that when cells isolated by treating protease or the artificial skin (epidermal cells or dermal cells, or the artificial skin composed of both cells) are frozen at −80° C., the cells are damaged and applied to the wounds to reduce the therapeutic effect (Tissue eng 4(4):1403-414, 1988).

However, in the mesenchymal stem cells-hydrogel-biodegradable or nondegradable support sheet prepared according to the present invention, the hydrogel covers the stem cells to protect the cells from external impact and stress, thereby enabling long-term storage without damage on the cells even at −80° C.

In one embodiment of the present invention, an effective does of one or more growth factors, cytokines, hormones or extracellular matrix compounds or proteins useful for enhancing the effect of alleviating or improving epidermolysis bullosa may be administered with the composition according to the present invention. Specifically, the examples may include GCSF, IL6, IL8, IL10, MCP1, MCP2, tissue factor, bFGF, KGF, VEGF, PLGF, MMP1, MMP9, TIMP1, TIMP2, TGF-β1, HGF, and the like, but are not limited thereto.

Hereinafter, the present invention will be described in more detail through Examples. However, these Examples are just examples of the present invention and the scope of the present invention is not limited thereto.

Example 1: Method of Culturing Human Adipose-Derived Mesenchymal Stem Cells

Adipose tissue may be usually obtained by liposuction, but is not limited thereto. Adipose-derived mesenchymal stem cells were isolated from the adipose tissue obtained by liposuction as follows: To remove blood, the adipose tissue was washed, and then added with the same volume of collagenase solution as the adipose tissue thereto, and reacted at 37° C. in a water bath.

After the centrifugation, the fat layer as a supernatant was removed, and the collagenase solution as the lower layer was carefully isolated without shaking, suspended in a substrate medium, and then centrifuged at 20° C. and 1500 rpm for 5 minutes. At this time, the lower layer served as the stroma-vascular fraction, and the supernatant was removed. The stroma-vascular fraction was suspended in the substrate medium, inoculated into a culture vessel, and cultured in a 5% $CO_2$ incubator at 37° C. for 24 hours.

After the removal of the culture medium, the cells were washed with a phosphate buffer solution and proliferated using the substrate medium, a growth medium containing the bFGF at a concentration of 1 ng/mL in the substrate medium, or a medium containing EGF at a concentration of 5 ng/mL in the substrate medium. The adipose-derived mesenchymal stem cells were grown about 80 to 90% of the culture vessel and then treated with trypsin to be isolated and obtained to single cells.

Example 2: Determination of Concentration of Fibrin Glue as Hydrogel

Lyophilized thrombin was added to 1 mL of a calcium chloride solution to be 400 to 600 I.U. Alternatively, the frozen thrombin was thawed and adjusted to the same concentration, and then used. The lyophilized thrombin was added with 1 mL of an aprotinin solution or thawed to prepare a undiluted solution and then the undiluted solution was diluted stepwise to 1:5, 1:10, 1:20, and 1:40. The cells subcultured two times or more in Example 1 were collected and suspended, mixed with thrombin at a ratio (v/v) of 40 to 50:1, and then mixed with fibrigen diluted stepwise at 1:1 to form a fibrin gel. When the gel was completely hardened, the cells were added with a culture medium containing 10% FBS and 1 ng/mL bFGF and cultured in a 5% $CO_2$ incubator at 37° C. for 5 days.

On the 2nd and 5th day of the culture, the cell-fibrin gel mixture was taken and made into thin slices, stained with 10 μg/mL of acridine orange/ethidium bromide (AO/EtBr), and a form and a survival rate of the cells were measured using a fluorescence microscope. Also, on the 5-th day of the culture, WST-1 was added to measure a cell growth degree.

FIG. 1A is a micrograph showing the forma and the number of stem cells in a fibrin gel prepared from a undiluted solution or a diluted fibrinogen solution. In the fibrin gel made from the fibrinogen undiluted solution, most of the cells kept a spherical cell shape until the 5th day and were almost not proliferated. On the other hand, as the dilution ratio increased, the cells rapidly formed fibroblast shapes and were proliferated more. Some dead cells were observed in the fibrin gel prepared from the undiluted fibrinogen, but no dead cells were observed in the fibrin gel prepared with the diluted fibrinogen. That is, the high-concentration fibrin gel shows weak cytotoxicity to the adipose-derived mesenchymal stem cells, but the fibrin gel at a dilution of 1:5 to 1:40 has no cytotoxicity.

Figure 1B:
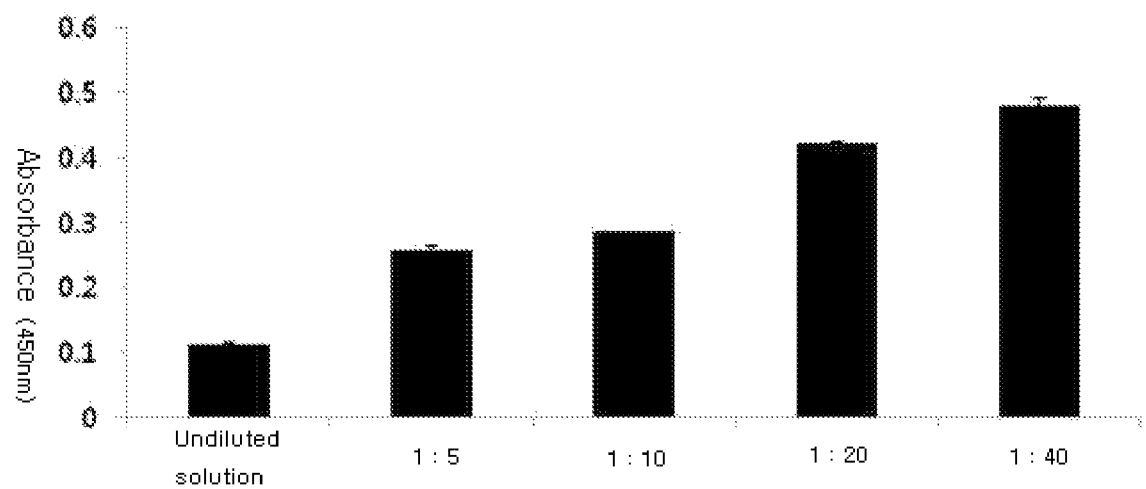
FIG. 1B is a graph of absorbance measured by adding WST-1 to mesenchymal stem cells derived from the human adipose which are cultured by mixing a fibrinogen undiluted solution and a fibrin gel prepared by a solution diluted stepwise.

FIG. 1B is a graph showing quantitative measurement of the growth activity of stem cells according to the fibrinogen gel using WST-1, in which as the dilution rate increases, the absorbance increases. In other words, it can be seen that the stem cells are proliferated best in the fibrin gel prepared by diluting the fibrinogen 20 or 40 times.

Example 3: Preparation of Human Adipose-Derived Mesenchymal Stem Cells-Hydrogel-Biodegradable or Nondegradable Support Sheet The mesenchymal stem cells subcultured two times or more in Example 1 were collected and suspended in the growth medium. Based on the results of Example 2, thrombin was added to the cell suspension to be a final 8 to 15 I.U.

The fibrinogen at a concentration of about 3 to 6.5 mg/mL was applied evenly on vicryl mesh or bovine placental membrane as a biodegradable support having a square shape of about 5×5 cm or gauze, polyurethane coated with soft silicon on a single surface, and a PET film as a nondegradable support, as a support. Thereafter, the cell suspension containing thrombin was applied to the support to have about 5,000 cells per $cm^2$, and then the cell-fibrin gel was uniformly formed and attached to the support. When the fibrin gel was completely hardened, the cells were added with a growth medium and cultured at 37° C. in a 5% $CO_2$ incubator for 3 to 7 days.

Figure 2A:
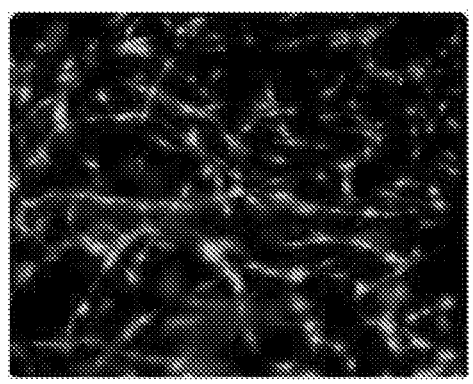
FIG. 2A is a photograph obtained by culturing a human adipose-derived mesenchymal stem cells-hydrogel-biodegradable support or nondegradable support sheet for 5 days, staining cells in the sheet with AO/EtBr, and observing the stained cells by a fluorescence microscope, as a photograph of cells in the sheet.
Figure 2B:
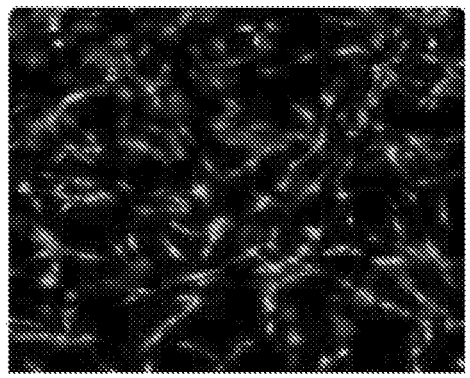
FIG. 2B is a photograph obtained by freezing at −80° C. and thawing the human adipose-derived mesenchymal stem cells-hydrogel-biodegradable support or nondegradable support sheet, staining cells in the sheet with AO/EtBr, and observing the stained cells by a fluorescence microscope.

FIG. 2A is a photograph of a sheet which is prepared by mixing human adipose-derived mesenchymal stem cells with a fibrin hydrogel and attaching and culturing the mesenchymal stem cells-fibrin hydrogel to polyurethane coated with soft silicon on a single surface and a PET film as nondegradable supports and then observed by a fluorescence microscope after AO/EtBr staining. FIG. 2B is a photograph of the sheet frozen at −80° C. which is thawed and then observed by a microscope or a fluorescence microscope after AO/EtBr staining. As illustrated in FIG. 2B, it was observed that even after thawing after freezing, the cells in the form of fibroblasts similar to those before freezing were attached to the support by the hydrogel and proliferated. About 20,000 to 400,000 cells per 1 $cm^2$ of the sheet were uniformly distributed and 100% survived.

Example 4: Freezing of Human Adipose-Derived Mesenchymal Stem Cells-Hydrogel-Biodegradable or Nondegradable Support Sheet The human adipose-derived mesenchymal stem cells-hydrogel-biodegradable or nondegradable support sheet prepared in Example 3 was washed to remove a cell culture medium, put in a Cryovac containing a freeze preservative (a solution containing 10% DMSO and human serum albumin), and then frozen at −80° C. After about 1 month, 3 months, 6 months, 9 months, and 12 months, the Cryovac was taken out for each period and immersed in a constant temperature water bath at 37° C., and then shaken to dissolve and remove the freeze preservative. Physiological saline was added and then shaken up and down and removed. After the freeze preservative was completely removed, the cells were stained by AO/EtBr to measure a survival rate.

Figure 3:
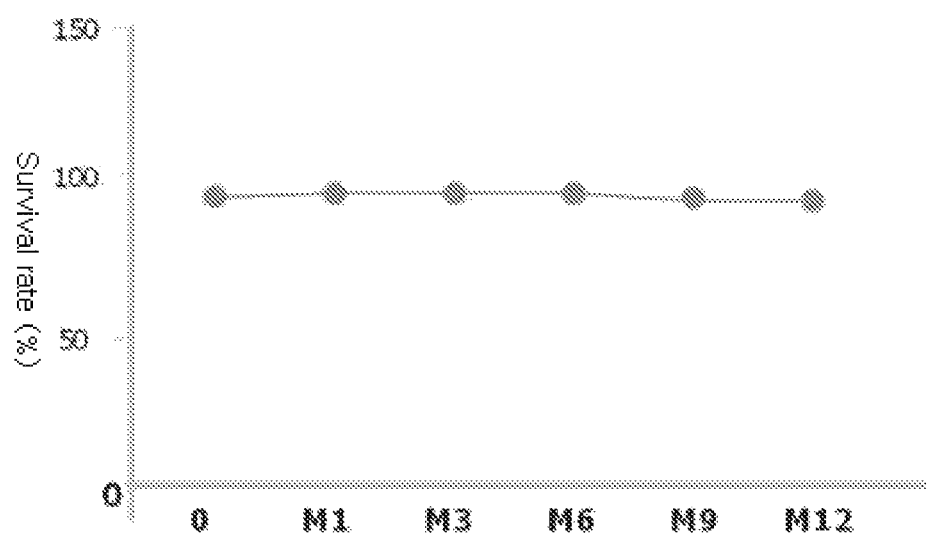
FIG. 3 is a photograph showing survival rate of cells in the sheet after freezing the sheet at −80° C. and thawing the sheet for 1, 3, 6, 9, and 12 months in order to evaluate long-term storage stability of the human adipose-derived mesenchymal stem cells-hydrogel-biodegradable support or nondegradable support sheet.

As a result, as illustrated in FIG. 3, 95% or more of the adipose-derived mesenchymal stem cells survived until 12 months in the sheet prepared according to the present invention.

That is, it is shown that the human adipose-derived mesenchymal stem cells-hydrogel-biodegradable or nondegradable support sheet prepared according to the present invention may be frozen for a long time at −80° C. without the damage on cells as a main active ingredient.

Figure 4A:
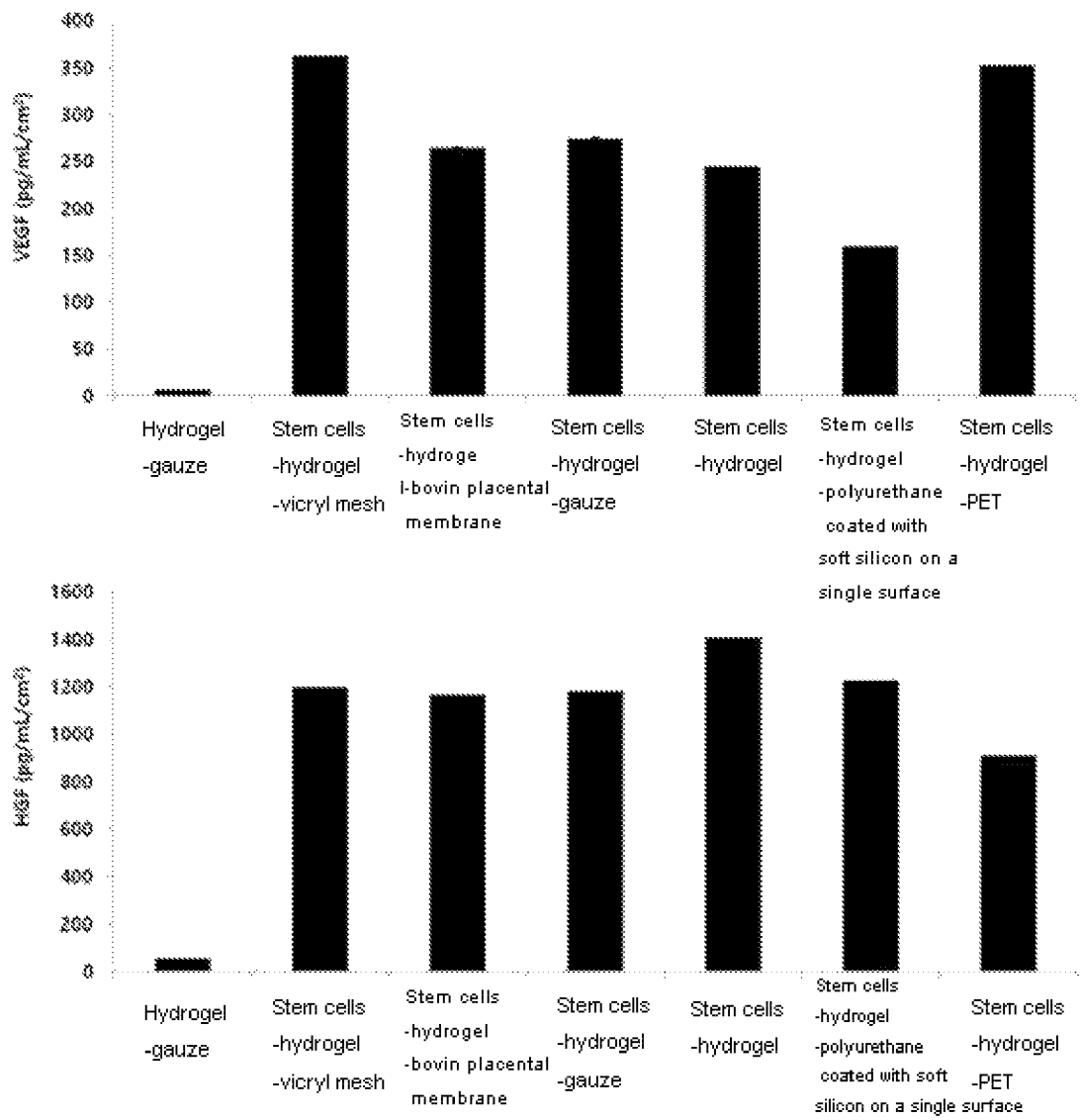
FIG. 4A is a graph showing amounts of VEGF and HGF secreted from the human adipose-derived mesenchymal stem cells-hydrogel-biodegradable support or nondegradable support sheet which are measured by ELISA.

Example 5: Secretion of Growth Factors of Human Adipose-Derived Mesenchymal Stem Cells-Hydrogel-Biodegradable or Nondegradable Support The human adipose-derived mesenchymal stem cells-hydrogel-biodegradable or nondegradable support sheet in Example 3 or the frozen sheet in Example 4 was thawed, washed with PBS, and then cut with sizes of 0.8×0.8 cm, and then two sheets were put in a 24-well plate and added with DMEM 1 mL. After culturing in a 5% $CO_2$ incubator at 37° C. for 72 hours, the supernatant was collected and the amounts of VEGF and HGF, which were representative growth factors secreted from the mesenchymal stem cells, were measured by ELISA. As a result, as illustrated in FIG. 4A, the sheet secreted the HGF and the VEGF.

Figure 4B:
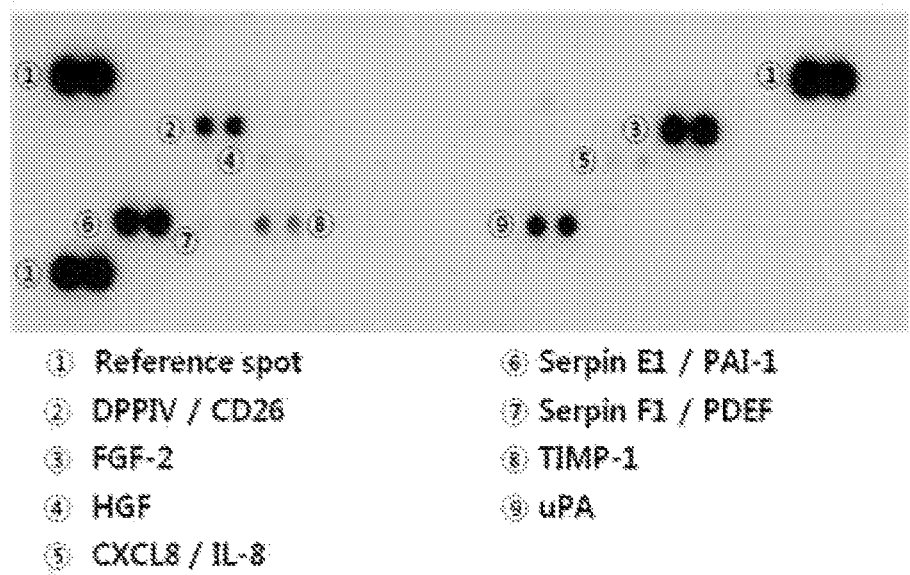
FIG. 4B is a diagram showing a result of analyzing angiogenesis promoting factors secreted from the human adipose-derived mesenchymal stem cells-hydrogel-biodegradable support or nondegradable support sheet using a cytokine array kit.

As another example, the collected supernatant was analyzed using a cytokine array kit associated with angiogenesis. As a result, as illustrated in FIG. 4B, the sheet secreted large amounts of growth factors including HGF and VEGF promoting angiogenesis and various cytokines such as serprinE1 (PAI-1), F1 (PDEF), TIMP-1, CXCL8 (IL-8), FGF-2, and DPPIV (CD26). That is, when the mesenchymal stem cells cultured using the hydrogel and the biodegradable or nondegradable support prepared according to the present invention were applied to the wounded part, it was found that various growth factors and cytokines promoting cell proliferation and angiogenesis were continuously secreted to activate peripheral tissue cells and alleviate or improve the epidermolysis bullosa.

Example 6: Immunoregulatory Function of Homogeneous Human Adipose-Derived Mesenchymal Stem Cells-Hydrogel-Biodegradable or Nondegradable Support The human adipose-derived mesenchymal stem cells-hydrogel-biodegradable or nondegradable support sheet in Example 3 or the frozen sheet in Example 4 was thawed, cut with appropriate sizes, and then one cut sheet was put in a 24-well plate. In addition, $5\times10^5$ peripheral blood mononuclear cells (PBMCs) obtained from donors having different human leukocyte antigens (HLA) were added in a 24-well plate. As a positive control, phyto-hemagglutinin as mitogen was added to the PBMCs to cause an immune response of the PBMCs. On the 3th day after the start of the response, the supernatant was collected and the amount of secreted TNF-α was measured by an ELISA method.

As yet another Experimental Example, $5\times10^5$ PBMCs were put in the 24-well plate and activated by PHA to cause the immune response, the homogeneous human adipose-derived mesenchymal stem cells-hydrogel-biodegradable or nondegradable support sheet prepared in Example 3 or 4 was cut with appropriate sizes, and then one cut sheet was added to the plate. On the 3th day of the response, the supernatant was collected and the secretion amount of TNF-α was measured.

Figure 5:
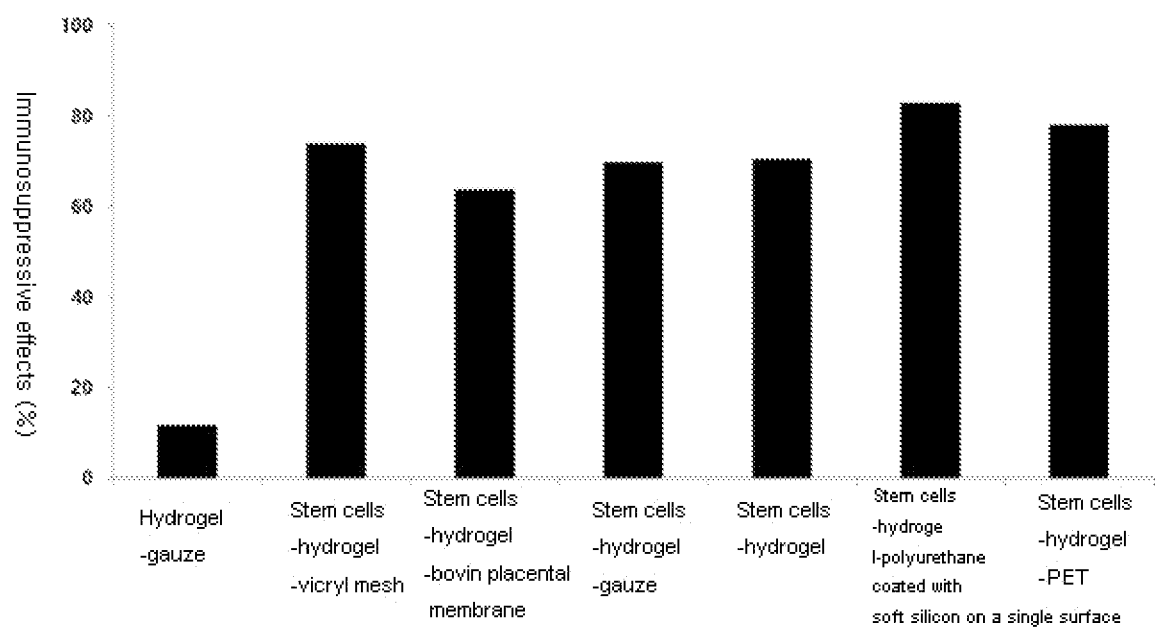
FIG. 5 is a graph showing an amount of TNF-α secreted from peripheral blood mononuclear cells after co-culturing the human adipose-derived mesenchymal stem cells-hydrogel-biodegradable support or nondegradable support sheet with homologous activated peripheral blood mononuclear cells, which is measured by ELISA and converted to a secretion inhibition rate (%) of TNF-α.

As a result, as illustrated in FIG. 5, in the PBMCs activated by PHA, the homogeneous human adipose-derived mesenchymal stem cells-hydrogel-biodegradable or nondegradable support sheet reduced the secretion amount of TNF-α by 60% or more. That is, the homogeneous human adipose-derived mesenchymal stem cells-hydrogel-biodegradable or nondegradable support sheet does not cause the immune response. Also, when an excessive immune response occurs, the sheet serves to significantly reduce the secretion amount of TNF-α which is secreted in large amount by immune cells and serves to increase immunoreactivity. Accordingly, the adipose-derived mesenchymal stem cells-hydrogel-biodegradable or nondegradable support sheet covers the wounded part of epidermolysis bullosa to continuously alleviate the inflammation and promote re-epithelization.

Example 7: ECM Secretion Ability of Human Adipose-Derived Mesenchymal Stem Cells Proteins were extracted from the cells obtained in Example 1 and expression levels of collagen type VII and laminin 5 as causative proteins of epidermolysis bullosa were measured by a Western blot method and then compared with expression levels in fibroblasts. Further, the expression level and the secretion amount were measured by an ELISA method from the human adipose-derived mesenchymal stem cells which were a raw material of the sheet prepared in the present invention.

Figure 6A:
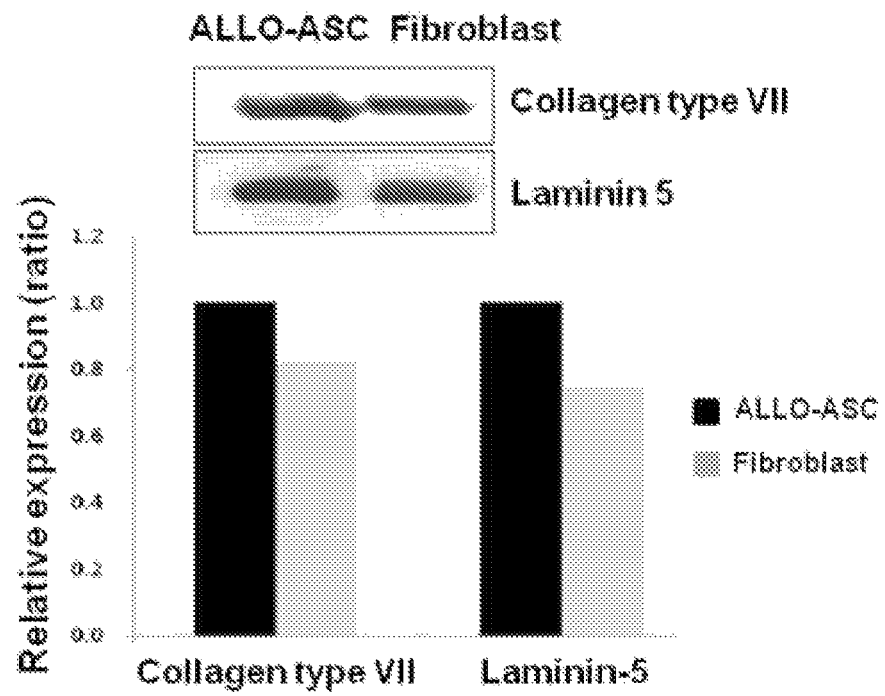
FIG. 6A is a diagram showing the results of verifying expression levels of collagen type VII and laminin among extracellular matrix proteins expressed by human adipose-derived mesenchymal stem cells and fibroblasts through Western blot.
Figure 6B:
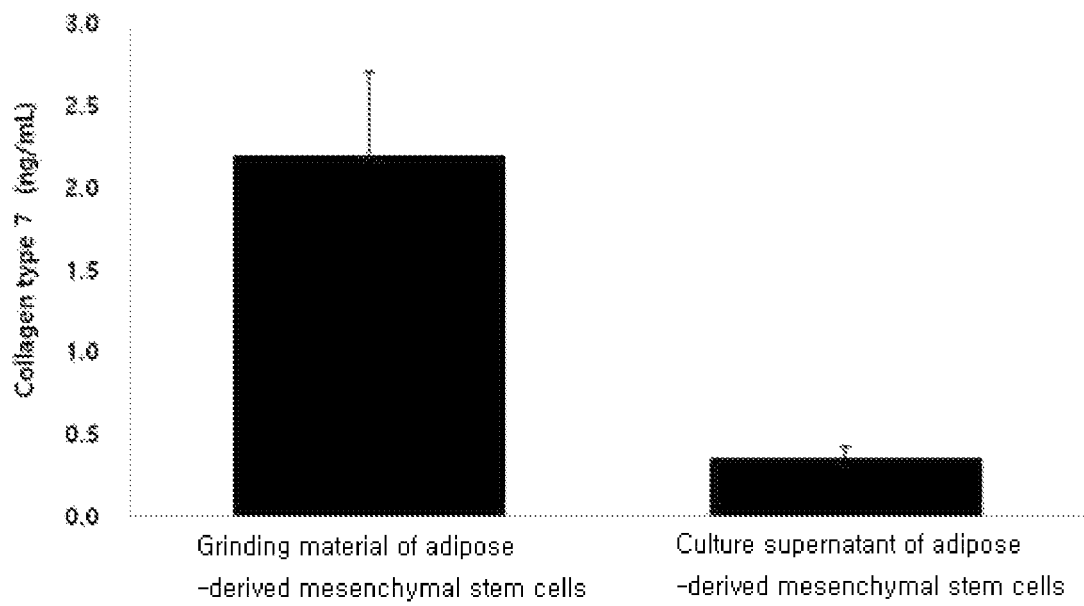
FIG. 6B is a graph showing results of verifying the expression level of collagen type VII of extracellular matrix proteins expressed in the human adipose-derived mesenchymal stem cells by ELISA.

FIG. 6A shows that the in the human adipose-derived mesenchymal stem cells which were a raw material of the sheet prepared in the present invention, expression levels of collagen type VII and laminin 5 are high as compared with the fibroblasts. FIG. 6B illustrates results of quantifying the amounts of collagen type VII expressed and secreted from the human adipose-derived mesenchymal stem cells.

As yet another example, the adipose-derived mesenchymal stem cells prepared in Example 1 were fixed and added with PBS containing a collagen type VII or collagen type I-specific antibody, and then reacted at 37° C. for 1 hour and washed, mounted, and observed by a fluorescence microscope.

Figure 6C:
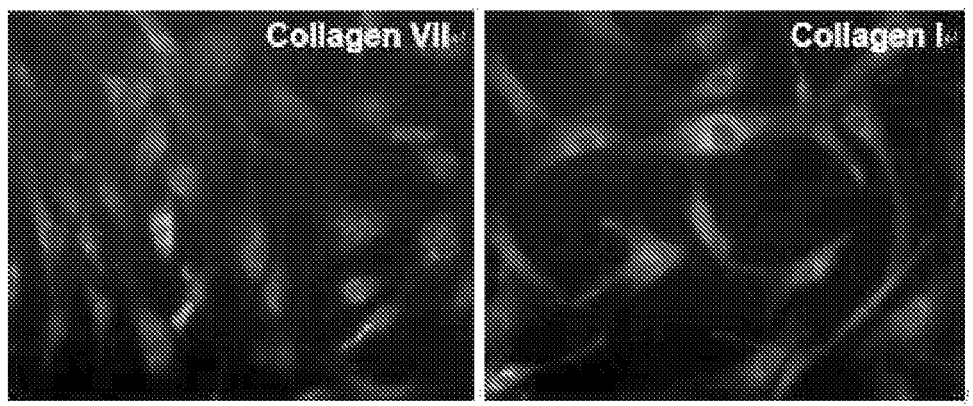
FIG. 6C is a photograph obtained by observing the expression levels of collagen type VII and of collagen type I extracellular matrix proteins expressed in the human adipose-derived mesenchymal stem cells by a fluorescence microscope after immunofluorescence staining.

FIG. 6C is a photograph (×400) showing secretion ability of extracellular matrix proteins of the adipose-derived mesenchymal stem cells, and as illustrated in FIG. 6C, the adipose-derived mesenchymal stem cells-hydrogel-biodegradable or nondegradable support prepared according to the present invention entirely had a positive reaction for collagen type VII and collagen type I.

Example 8: Evaluation of ECM Secretion and Expression of Human Adipose-Derived Mesenchymal Stem Cells-Hydrogel-Biodegradable or Nondegradable Support The human adipose-derived mesenchymal stem cells-hydrogel-biodegradable or nondegradable support prepared in Example 3 or 4 was cultured in a DMEM without adding FBS for 3 days and then the culture medium was collected to measure ECM secretion ability and expression rate by an ELISA method.

Figure 7A:
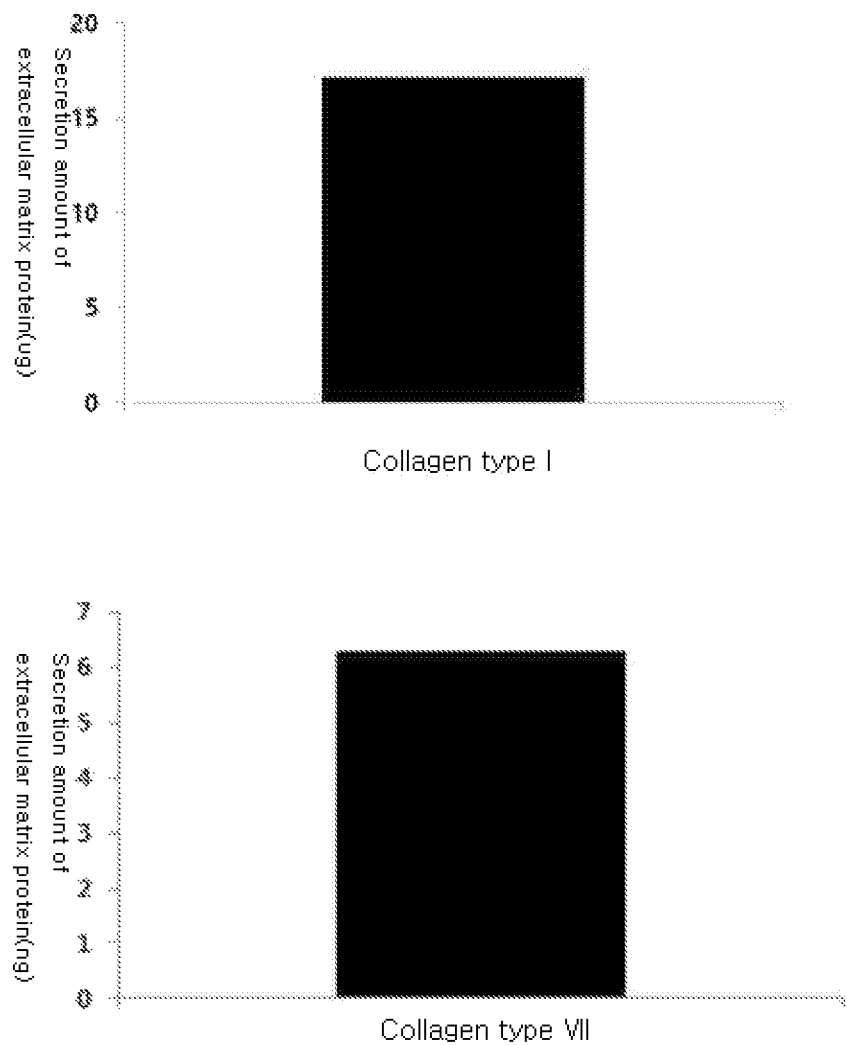
FIG. 7A is a graph showing amounts of collagen type VII and collagen type I which are extracellular matrix proteins secreted from the sheet according to the present invention.

As a result, as illustrated in FIG. 7A, the adipose-derived mesenchymal stem cells-hydrogel-biodegradable or nondegradable support prepared according to the present invention secreted collage types VII and I.

As yet another example, frozen slices of the adipose-derived mesenchymal stem cells-hydrogel-biodegradable or nondegradable support prepared in Example 3 or 4 were made and fixed, added with an extracellular matrix protein-specific antibody, reacted at 37° C. for 1 hour, washed, mounted, and then observed by a fluorescence microscope.

Figure 7B:
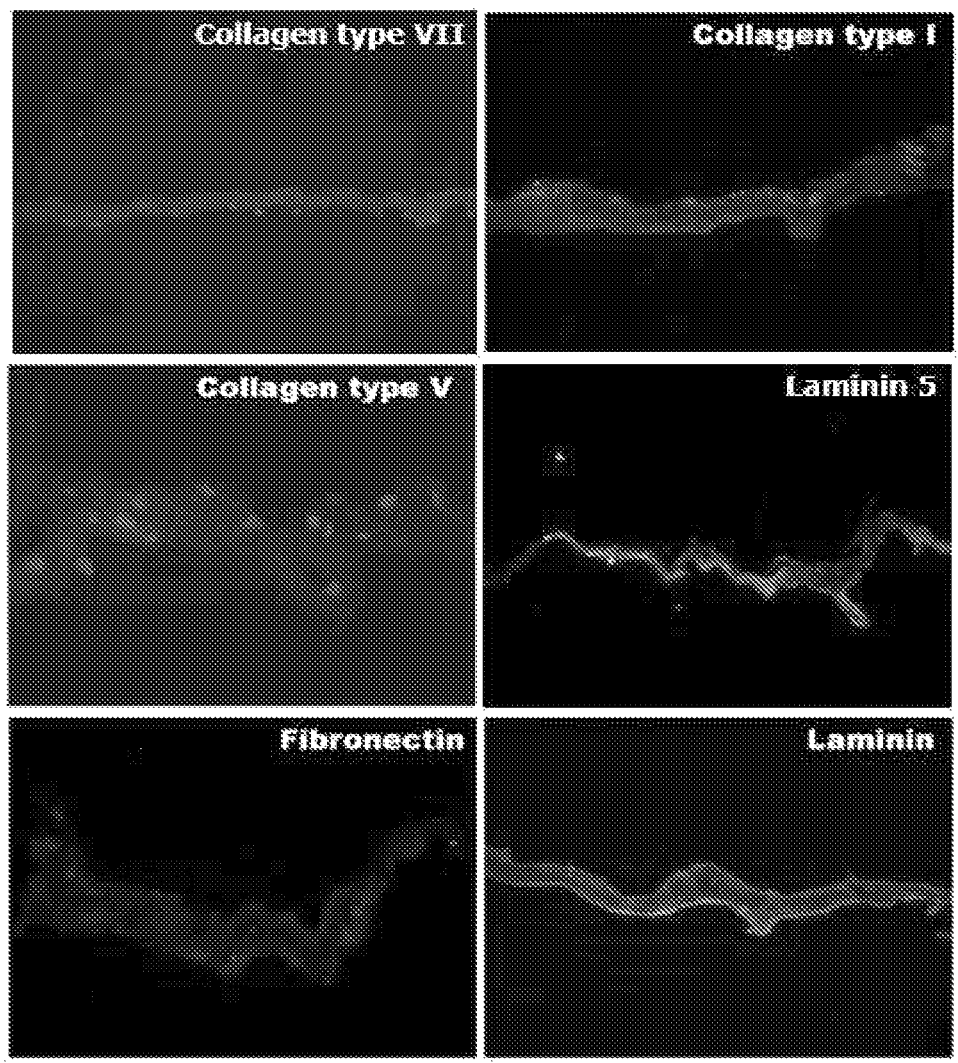
FIG. 7B is a photograph showing the expression levels of collagen type VII, collagen type I, collagen type V, laminin 5, fibronectin, laminin, and the like which are extracellular matrix proteins included in the sheet according to the present invention by a fluorescence microscopy after immunofluorescence staining.

As a result, as illustrated in FIG. 7B, the adipose-derived mesenchymal stem cells-hydrogel-biodegradable or nondegradable support prepared according to the present invention had a positive reaction for collage type VII, collage type I, collage type V, laminin 5, fibronectin, and laminin. That is, the cells configuring the adipose-derived mesenchymal stem cells-hydrogel-biodegradable or nondegradable support prepared according to the present invention secreted various types of extracellular matrix proteins in large amount and the secreted extracellular matrix proteins were left in the hydrogel and transplanted into the body to provide various substrates, thereby alleviating or improving epidermolysis bullosa.

Figure 8:
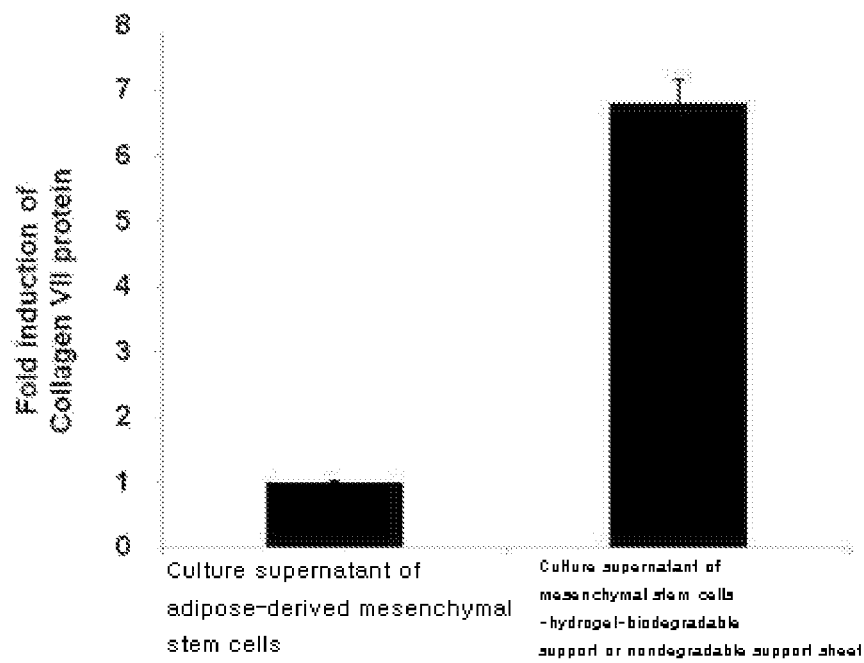
FIG. 8 is a graph obtained by comparing an amount of collagen type VII which is an extracellular matrix protein secreted from human adipose-derived mesenchymal stem cells which are monolayer-cultured with the sheet according to the present invention.

Example 9: Expression of Collage Type VII of Human Adipose-Derived Mesenchymal Stem Cells and Human Adipose-Derived Mesenchymal Stem Cells-Hydrogel-Biodegradable or Nondegradable Support FIG. 8 illustrates results of secretion ability of adipose-derived mesenchymal stem cells single-layer cultured according to an existing culture method and extracellular matrix proteins of the adipose-derived mesenchymal stem cells in the sheet, and in the adipose-derived mesenchymal stem cells-hydrogel-biodegradable or nondegradable support prepared according to the present invention, collagen type VII was secreted 6.8 times larger than that of the existing single-layer cultured cells.

As the above result, when the adipose-derived mesenchymal stem cells-hydrogel-biodegradable or nondegradable support is attached to the wounded part of a patient with epidermolysis bullosa, the adipose-derived mesenchymal stem cells-hydrogel-biodegradable or nondegradable support supplies various extracellular matrix proteins to a skin damaged part, thereby promoting tissue regeneration and re-epithelization.

Example 10: Evaluation of Expression of Collagen Type VII in Human Adipose-Derived Mesenchymal Stem Cells by Inflammatory Material The cells obtained in Example 1 were added to a 12-well plate at $5,500/cm^2$, and after 24 hours, TGF-β2 and TNF-α were added and further cultured for 48 hours. After the cells were collected, RNA was extracted and the expression level of collagen type VII, which was a causative gene of epidermolysis bullosa, was measured by a RT-PCT method and the expression changes were compared with each other.

Figure 9:
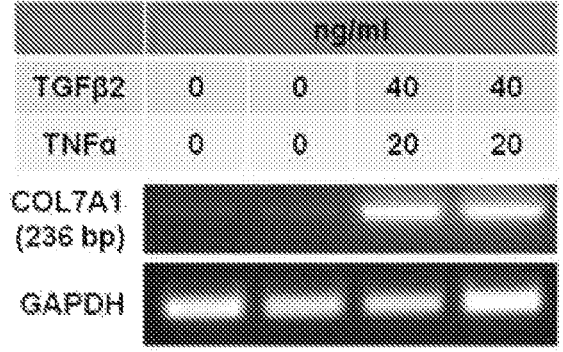
FIG. 9 is a diagram showing results that expression of collagen type VII is rapidly increased when human adipose-derived mesenchymal stem cells are exposed to inflammatory cytokines TGF-β2 and TNF-α secreted from a wounded part.
Figure 9:
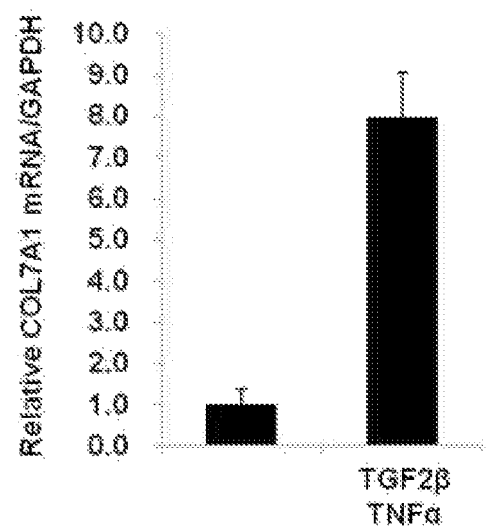

As a result, as illustrated in FIG. 9, when TGF-β2 and TNF-α were treated to the adipose-derived mesenchymal stem cells as a main ingredient of the sheet, the expression of collagen type VII increased about 8 times. As the above result, when the adipose-derived mesenchymal stem cells-hydrogel-biodegradable or nondegradable support prepared according to the present invention is attached to the wounded part of a patient with epidermolysis bullosa, the expression level of collagen type VII of the adipose-derived mesenchymal stem cells-hydrogel-biodegradable or nondegradable support is increased by inflammatory materials existing in a chronic skin damaged part, thereby promoting tissue regeneration and re-epithelization.

Example 11: Restoring the Morphology, Adherence Ability, Mobility of Collagen Type VII Deficient Fibroblasts by Human Adipose-Derived Mesenchymal Stem Cells-Hydrogel-Biodegradable or Nondegradable Support In order to evaluate whether the adipose-derived mesenchymal stem cells-hydrogel-biodegradable or nondegradable support in Example 4 can restore the function of collagen type VII deficient cells, fibroblasts were treated with siRNA to induce deficiency of collagen type VII.

Figure 10:
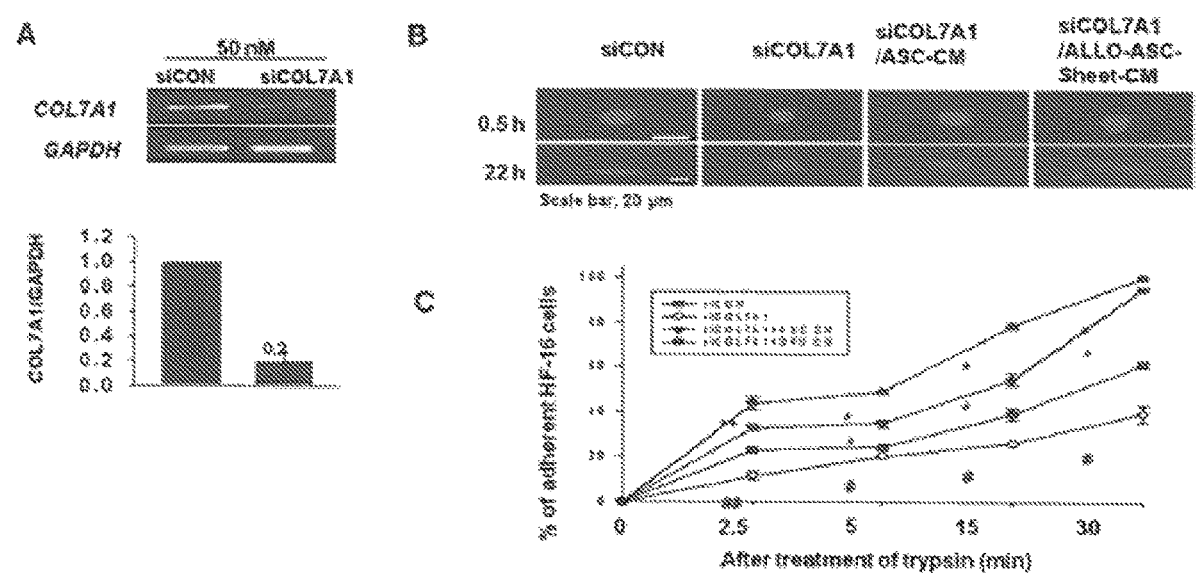
FIG. 10 is a diagram showing results that the sheet according to the present invention restores the morphology and adherence of collagen type VII deficient fibroblasts.

As illustrated in FIG. 10, the collagen type VII deficient fibroblasts kept in a round shape without being attached to the bottom of the culture vessel after 24 hours being inoculated into the culture vessel. However, as a result of treating 72 hours of conditioned media (CM) of the adipose-derived mesenchymal stem cells-hydrogel-biodegradable or nondegradable support, the collagen type VII deficient cells adhered to the bottom of the culture vessel and the collagen type VII deficient cells restored the fusiform shape similar to normal cells.

Figure 11:
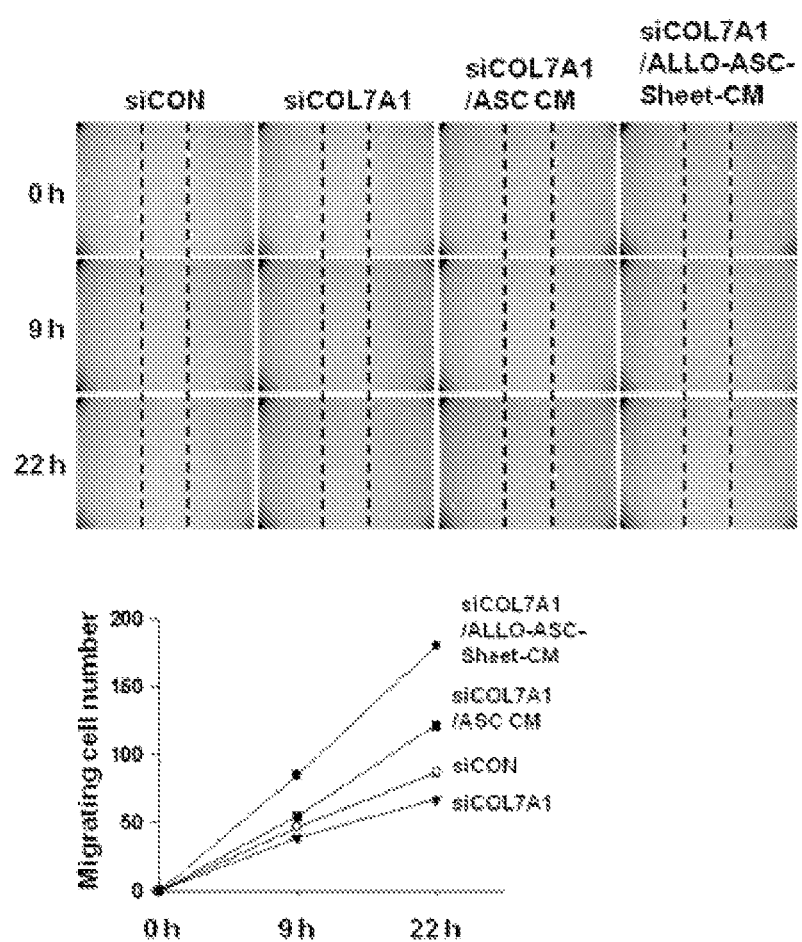
FIG. 11 is a diagram showing results that the sheet according to the present invention can regenerate a skin by restoring the mobility of the collagen type VII deficient fibroblasts.

As another example, fibroblasts were attached to the bottom of the culture vessel and cultured, and then treated with siRNA to induce collagen type VII deficiency. As a result that scratch (wound) model was made by scraping the center of the cultured cells and mobility of the scratch model to scratch area was evaluated, the mobility of collagen type VII deficient fibroblasts was decreased compared to normal fibroblasts. Here, when treating adipose-derived mesenchymal stem cells-hydrogel-biodegradable or nondegradable support CM, migration of collagen type VII deficient cells was promoted as shown in FIG. 11.

As the above result, it can be seen that the adipose-derived mesenchymal stem cells-hydrogel-biodegradable or nondegradable support can restore the function of collagen type VII deficient cells and effectively restore the skin tissue.

Example 12: Treatment Example of Epidermolysis Bullosa by Human Adipose-Derived Mesenchymal Stem Cells-Hydrogel-Biodegradable or Nondegradable Support In order to evaluate a therapeutic effect of the adipose-derived mesenchymal stem cells-hydrogel-biodegradable or nondegradable support prepared in Example 4, clinical trials were conducted in a patient with epidermolysis bullosa.

This patient was a 24-year-old female patient and diagnosed as epidermolysis bullosa, but since there was not separate therapeutic method, there was no improvement in the disease due to continuous recurrence and inflammation. The adipose-derived mesenchymal stem cells-hydrogel-biodegradable or nondegradable support prepared in Example 4 was attached to the wounded part of the patient and photographed and observed at an interval of 1 week, and then a wound treatment effect was evaluated.

Figure 12:
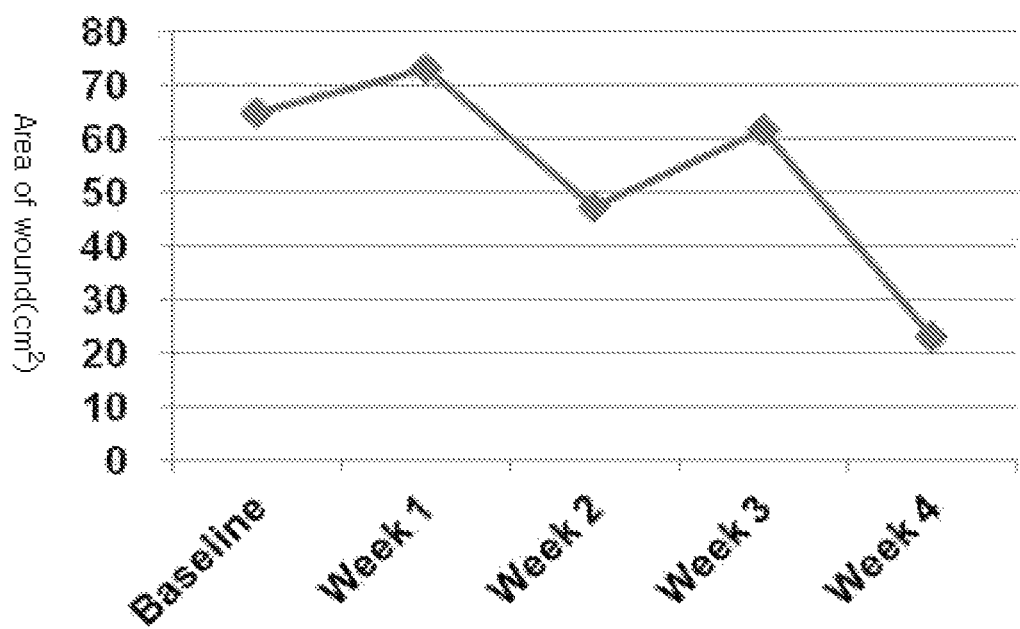
FIG. 12 is a graph showing changes in the size of the wounded part for a total of 4 weeks before and after attaching the sheet according to the present invention to a patient with epidermolysis bullosa.

FIG. 12 is a graph showing a wound area after attaching the adipose-derived mesenchymal stem cells-hydrogel-biodegradable or nondegradable support, and as the time elapsed after attaching the adipose-derived mesenchymal stem cells-hydrogel-biodegradable or nondegradable support prepared according to the present invention, the wound area was reduced, and after 4 weeks of the attachment, the wound area was reduced by 64.4% as compared with before attachment.

That is, it can be seen that the adipose-derived mesenchymal stem cells-hydrogel-biodegradable or nondegradable support prepared according to the present invention secreted various types of extracellular matrix proteins in large amount, and the secreted extracellular matrix proteins were left in the hydrogel and transplanted into the body to provide various substrates, thereby alleviating or improving epidermolysis bullosa.

INDUSTRIAL AVAILABILITY

The composition or sheet for alleviating or improving epidermolysis bullosa, containing the mesenchymal stem cells-hydrogel-biodegradable support or nondegradable support according to the present invention increases the expression of specifically, collagen type VII and laminin-5 to express a clinically significant effect when being applied to the wounded part of epidermolysis bullosa. Therefore, the composition or sheet may be usefully used for alleviating or improving symptoms of a patient with epidermolysis bullosa.

What is claimed is:

1. A method for alleviating or improving epidermolysis bullosa, comprising applying a sheet as a dressing agent on a wounded part of skin present on a subject having epidermolysis bullosa so as to promote skin reproduction and re-epithelization at the wounded part, wherein the sheet comprises:

a composition comprising adipose-derived mesenchymal stem cells, a hydrogel, and an extracellular matrix comprising collagen type VII due to its expression and secretion by the adipose-derived mesenchymal stem cells;

wherein the composition is provided on a support that is at least one biodegradable support, at least one nondegradable support, or any combination thereof;

wherein the hydrogel is selected from the group consisting of fibrin glue, hyaluronic acid, gelatin, collagen, alginic acid, cellulose, and pectin;

wherein the biodegradable support is selected from the group consisting of poly-gamma-glutamic acid (PGA), poly lactic acid (PLA), vicryl mesh, human placental membrane, bovine placental membrane, pig collagen, chitin, chitosan, fibronectin, and dextran, wherein the nondegradable support is selected from the group consisting of sterilized nonwoven fabrics, polyethylene terephthalate (PET) films, polyethylene (PE) films, polypropylene (PP) films, polyurethane films, net type polyurethane films, and polyurethane coated with soft silicon on a single surface, and wherein the expression level of collagen type VII by the adipose-derived mesenchymal stem cells in the composition is higher than in fibroblasts with the same cell number as the adipose-derived mesenchymal stem cells.

2. The method of claim 1, wherein the composition is not pre-treated with TGF-β2 and TNF-α.

3. The method of claim 1, wherein the extracellular matrix further comprises laminin-5 due to its expression and secretion by the adipose-derived mesenchymal stem cells.

4. The method of claim 1, wherein the hydrogel is fibrin glue comprising fibrinogen at a concentration of 0.5 to 45 mg/mL.

5. The method of claim 4, wherein the fibrin glue comprises fibrinogen at a concentration of 0.5 to 10 mg/mL.

6. The method of claim 1, wherein the sheet comprises 20,000 to 400,000 of the adipose-derived mesenchymal stem cells per 1 cm$^2$ of the support.

7. The method of claim 1, wherein the epidermolysis bullosa is selected from the group consisting of epidermolysis bullosa, acantholysis bullosa, acanthosis bullosa, epidermolysis bullosa acquisita, epidermolysis bullosa hereditaria, epidermolysis bullosa letalis, epidermolysis bullosa tarda, epidermolysis hereditaria tarda, hyperplastic epidermolysis bullosa, keratolysis, localized epidermolysis bullosa, non-scarring epidermolysis bullosa, polydysplastic epidermolysis bullosa, scarring bullosa, simplex epidermolysis bullosa, Weber-Cockayne disease, Dowling-Meara syndrome, Goldscheider's disease, Hallopeau-Siemens disease, Heinrichsbauer syndrome, Herlitz syndrome, and Kobner's disease.

8. The method of claim 1, wherein the adipose-derived mesenchymal stem cells have a survival rate of 90% or more when thawing after freezing for 12 months or more.

9. The method of claim 1, wherein the adipose-derived mesenchymal stem cells have a fibroblast shape.

10. The method of claim 1, wherein the adipose-derived mesenchymal stem cells express CD29, CD44, CD73, CD90, and CD105.

11. The method of claim 1, wherein the extracellular matrix further comprises growth factors including VEGF and HGF due to their expression and secretion by the adipose-derived mesenchymal stem cells.

12. The method of claim 1, wherein the adipose-derived mesenchymal stem cells are positive for CD29, CD44, CD73, CD90, and CD105 and negative for CD34 and CD45.

13. The method of claim 1, wherein the adipose-derived mesenchymal stem cells are positive for CD10, CD13, CD29, CD44, CD59, CD71, CD90, CD105 and Oct4 and negative for CD34, CD45, CD104, CD106 and Stro-1.

14. The method of claim 1, wherein the composition is able to restore the function of collagen type VII deficient cells.

15. The method of claim 1, wherein the composition does not comprise bone marrow mesenchymal stem cells.

* * * * *